United States Patent
Ehr et al.

(10) Patent No.: US 6,409,728 B1
(45) Date of Patent: Jun. 25, 2002

(54) ROTATABLE BIPOLAR FORCEPS

(75) Inventors: Chris Ehr, Longmont, CO (US); Heinz Hluchy, Mössingen (DE); Valintina Arroyo, Erie, CO (US)

(73) Assignee: Sherwood Services AG, Schauffhausen (CH)

( * ) Notice: Subject to any disclaimer, the term of this patent is extended or adjusted under 35 U.S.C. 154(b) by 28 days.

(21) Appl. No.: 09/629,670

(22) Filed: Aug. 1, 2000

Related U.S. Application Data

(60) Provisional application No. 60/150,753, filed on Aug. 25, 1999.

(51) Int. Cl.$^7$ ............................................... A61B 18/18
(52) U.S. Cl. ............................. 606/51; 606/45; 606/205
(58) Field of Search ........................ 606/41, 42, 45–52, 606/205–208

(56) References Cited

U.S. PATENT DOCUMENTS

| | | |
|---|---|---|
| 2,002,594 A | 5/1935 | Wappler et al. |
| 2,518,994 A | 8/1950 | Miller |
| 3,938,527 A | 2/1976 | Rioux et al. |
| 5,116,332 A | 5/1992 | Lottick |
| 5,217,460 A | 6/1993 | Knoepfler |
| 5,258,006 A | 11/1993 | Rydell et al. |
| 5,275,615 A | 1/1994 | Rose |
| 5,282,800 A | 2/1994 | Foshee et al. |
| 5,330,471 A | 7/1994 | Eggers |
| 5,342,359 A | 8/1994 | Rydell |
| 5,443,479 A | 8/1995 | Bressi, Jr. |
| 5,456,684 A | 10/1995 | Schmidt et al. |
| 5,527,313 A | 6/1996 | Scott et al. |
| 5,637,110 A | 6/1997 | Pennybacker et al. |
| 5,755,717 A | 5/1998 | Yates et al. |
| 5,776,130 A | 7/1998 | Buysse et al. |
| 5,827,279 A * | 10/1998 | Hughett et al. .............. 606/205 |
| 5,951,549 A | 9/1999 | Richardson et al. |
| 6,068,647 A * | 5/2000 | Witt et al. ..................... 604/22 |
| 6,306,131 B1 * | 10/2001 | Hareyama et al. ............ 606/37 |

FOREIGN PATENT DOCUMENTS

| | | |
|---|---|---|
| CA | 2104423 | 8/1993 |
| EP | 0 584 787 A1 | 8/1993 |
| EP | 0 853 922 A1 | 10/1997 |

OTHER PUBLICATIONS

International Search Report—PCT/US99/24869.

The Mechanism of Blood Vessel Closure By High Frequency Electrocoagulation by Sigel and Dunn; *Surgery, Gynecology & Obstetrics*, Oct. 1965 pp. 823–831.

Studies on Coagulation and the Development of an Automatic Computerized Bipolar Coagulator by Bergdahl, Vallfors; *J. Neurosug*, vol. 75 Jul. 1991; pp. 148–151.

\* cited by examiner

*Primary Examiner*—Roy Gibson

(57) ABSTRACT

A rotatable bipolar forceps for clamping and coagulating tissue includes a body portion and an electrode which is selectively removable from the body portion. The forceps further includes at least one handle attached to the body portion for imparting movement to a shaft which causes the jaws to move from a first open position wherein the jaws are disposed in spaced relation relative to one another to a second clamping position wherein the jaws cooperate to grasp tissue therebetween. A rotating member rotates the electrode and the jaws relative to a longitudinal axis disposed through the body portion and releasably couples the electrode to the housing.

19 Claims, 4 Drawing Sheets

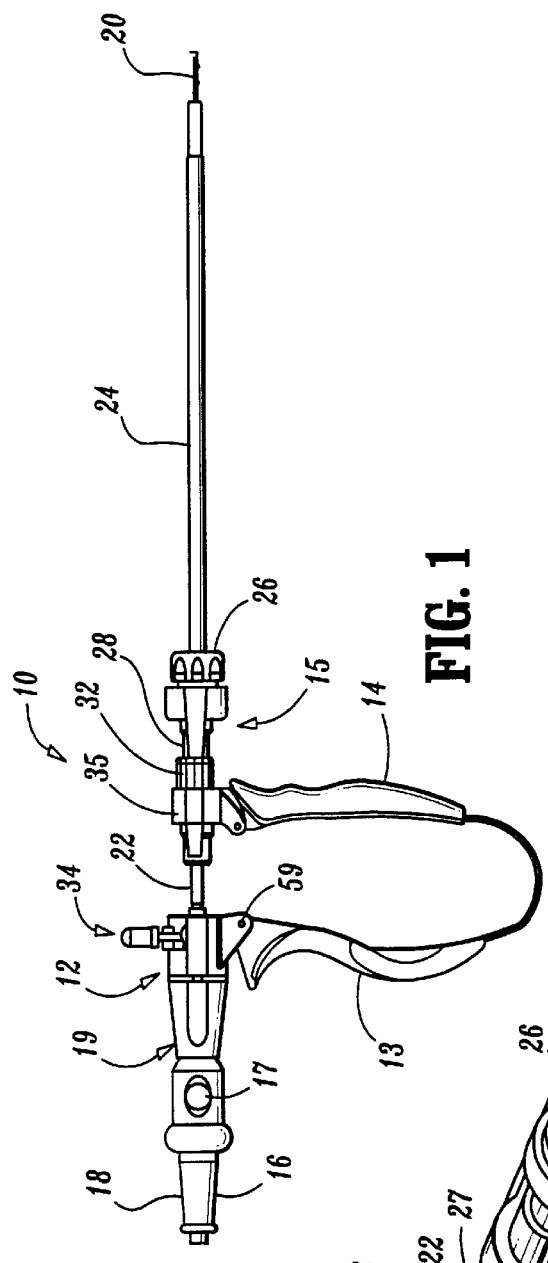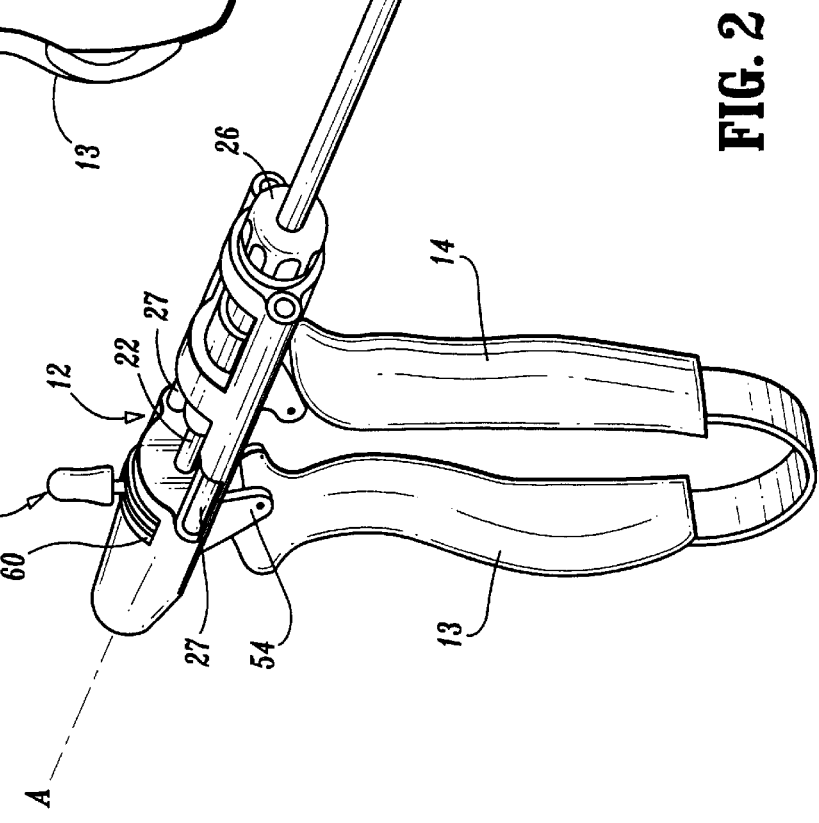

ROTATABLE BIPOLAR FORCEPS

This application claims priority from provisional application Ser. No. 60/150,753, filed Aug. 25, 1999.

BACKGROUND

The present disclosure relates to an electrosurgical instrument for performing minimally invasive endoscopic surgical procedures involving coagulation of body tissues. More particularly, the present disclosure relates to a reusable, rotatable endoscopic bipolar electrosurgical forceps which can be completely disassembled for sterilization and reuse.

TECHNICAL FIELD

A hemostat or forceps is a simple plier-like tool which uses mechanical action between its jaws to constrict vessels and is commonly used in open surgical procedures to grasp, dissect and/or clamp tissue. Electrosurgical forceps are similar clamping devices which utilize both mechanical clamping action and electrical energy to effect hemostasis by heating the tissue and blood vessels to cause coagulation and/or cauterization.

Over the last several decades, more and more surgeons are abandoning traditional open methods of gaining access to vital organs and body cavities in favor of endoscopes and endoscopic instruments which access organs through small puncture-like incisions. Endoscopic instruments are inserted into the patient through a cannula, or port, that has been made with a trocar. Typical sizes for cannulas range from three millimeters to twelve millimeters. Smaller cannulas are usually preferred which presents a design challenge to instrument manufacturers who must find ways to make surgical instruments that fit through these smaller cannulas.

Certain surgical procedures require cutting blood vessels or vascular tissue. However, due to space limitations surgeons can have difficulty suturing vessels or performing other traditional methods of controlling bleeding, e.g., clamping and/or tying-off transected blood vessels. Very small blood vessels, in the range below two millimeters in diameter, can often be closed using standard electrosurgical techniques. If a larger vessel is severed, it may be necessary for the surgeon to convert the endoscopic procedure into an open-surgical procedure and thereby abandon the benefits of laparoscopy.

By utilizing an electrosurgical forceps, a surgeon can either cauterize, coagulate/desiccate and/or cut tissue and/or simply reduce or slow bleeding, by controlling the intensity, frequency and duration of the electrosurgical energy applied to the tissue. Generally, the electrical configuration of electrosurgical forceps can be categorized in two classifications: 1) monopolar electrosurgical forceps; and 2) bipolar electrosurgical forceps.

Monopolar forceps utilize one active electrode associated with the clamping end effector and a remote patient return electrode or pad which is typically attached externally to the patient. When the electrosurgical energy is applied, the energy travels from the active electrode, to the surgical site, through the patient and to the return electrode.

Bipolar electrosurgical forceps utilize two generally opposing electrodes which are disposed on the inner opposing surfaces of the end effectors and which are both electrically coupled to an electrosurgical generator. Each electrode is charged to a different electric potential. Since tissue is a conductor of electrical energy, when the end effectors are utilized to grasp tissue therebetween, the electrical energy can be selectively transferred through the tissue. Typically, during surgery, the end effector must be manipulated at various angles of rotation depending upon the desired angle of cutting and/or coagulating. As a result, instruments have been developed which include rotatable end effectors which are rotated by a knob located in general proximity to the user's hand during operation.

It has also been found that cleaning and sterilizing many of the prior art bipolar instruments is often impractical as electrodes and/or insulation can be damaged. More particularly, it is known that electrically insulative materials, such as plastics, can be damaged or compromised by repeated sterilization cycles. Several instruments have been proposed in the past which are dismantleable and include replaceable components which facilitate cleaning and sterilization. However, it has been seen that as instruments increase in complexity, e.g., the addition of rotatable components, dismantling these instruments for cleaning and sterilization becomes difficult and often requires more than a rudimentary knowledge of the interworkings of the instrument and/or requires a series of intricate mechanical manipulations to disengage the more sensitive elements, e.g., the electrode.

Several bipolar endoscopic instruments are known which include rotatable elements and/or are dismantleable for cleaning purposes. For example, U.S. Pat. No. 5,716,354 to Hluchy discloses a rotatable bipolar instrument which includes a rotatable coupling and a separate knob which when depressed disengages the electrical tube from the instrument. A separate jack is used to rotate the instrument. U.S. Pat. No. 5,456,683 to Fritzsch et al. discloses a dismantleable medical instrument having a button for disengaging the electrical tube but is not rotatable.

Thus, a need exists to develop a rotatable bipolar instrument which is both simple to use and simple to assemble and disassemble for cleaning and sterilization purposes.

SUMMARY

The present disclosure relates to a rotatable bipolar forceps for clamping and coagulating tissue which includes a housing and an electrode which is selectively removable from the housing for connecting a pair of laws to a source of electrical energy. The forceps further includes at least one handle attached to the housing for imparting movement to a shaft which causes the jaws to move from a first open position wherein the jaws are disposed in spaced relation relative to one another to a second clamping position wherein the jaws cooperate to grasp tissue therebetween. A rotating member rotates the electrode and the jaws relative to a longitudinal axis disposed through the housing and releasably couples the electrode to the housing.

Preferably, the forceps further includes an outer shaft which is removably coupled to the housing and an inner shaft disposed within the outer shaft which is movable relative to the outer shaft upon movement of the handle. The inner shaft is preferably dimensioned to house the electrode therein and is insulated. It is envisioned that movement of the inner shaft relative to the outer shaft causes the jaws to move from the first position to the second position.

In one embodiment of the present disclosure, the rotating member includes a lever which couples to a distal end of the electrode and imparts rotational movement to the electrode. A spring-release mechanism or the like may be employed to releasably couple the lever to the electrode. Preferably, the lever rotates the electrode and, therefore, the jaws, about 60 degrees on either side of the longitudinal axis.

In another embodiment, the rotating member includes a guide clip which controls the rotational movement of the lever. Preferably, the guide clip includes an arcuately-shaped slot disposed therein for guiding the rotational movement of the lever. In one particular embodiment, a spring biases the lever in a normal position relative to the longitudinal axis.

BRIEF DESCRIPTION OF THE DRAWINGS

FIG. 1 is a side view of a bipolar forceps according to the present disclosure;

FIG. 2 is a perspective view of the bipolar forceps shown in FIG. 1;

DETAILED DESCRIPTION OF THE PREFERRED EMBODIMENTS

Figure 3:
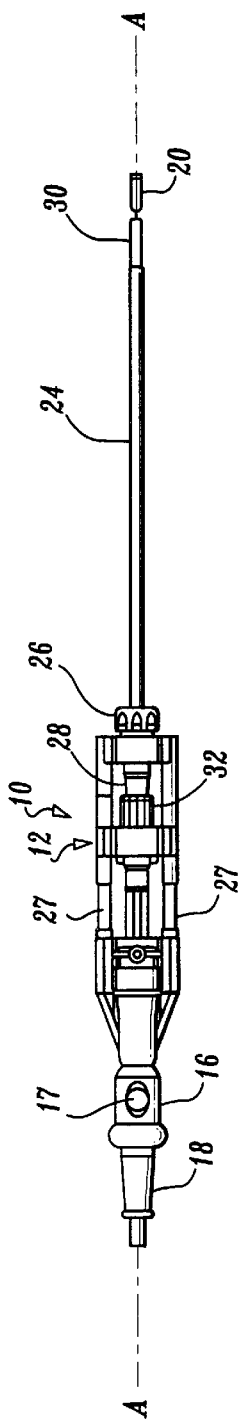
FIG. 3 is a top view of the bipolar forceps shown in FIG. 1.
Figure 4:
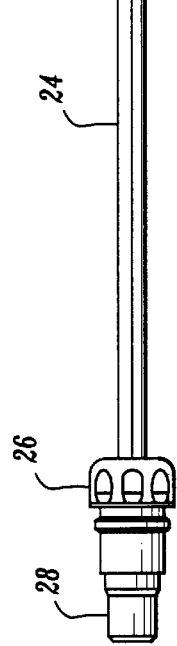
FIG. 4 is an enlarged, side view of the bipolar forceps of FIG. 1 showing an outer shaft which includes a sealing ring disposed at a proximal end of the shaft and a connecting screw disposed between the shaft and the sealing ring.
Figure 5:
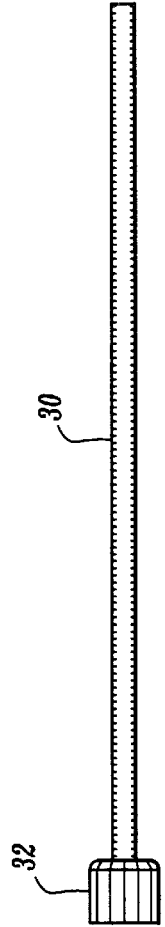
FIG. 5 is an enlarged, side view of the bipolar forceps of FIG. 1 showing an inner shaft which includes a connecting screw which couples the inner shaft to of forceps.
Figure 6:
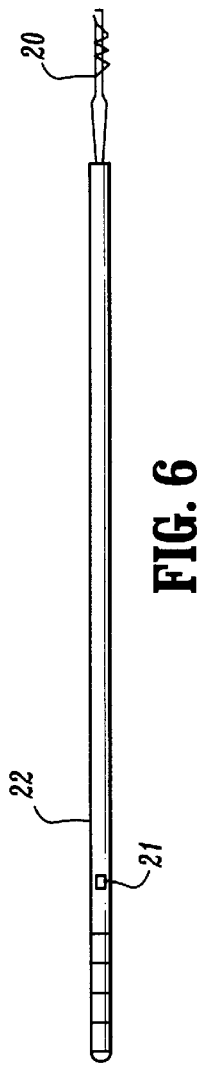
FIG. 6 is an enlarged, side view of the an electrode which is disposed within a central lumen of the inner shaft and which includes a proximal end which extends beyond the inner shaft to connect to the forceps and a distal end which receives a pair of coagulating jaws.

Referring now to FIGS. 1–6, a bipolar forceps 10 for use with minimally invasive surgical procedures involving the coagulation of body tissues includes a body portion 12 attached to actuating handles 13 and 14. Body portion 12 includes proximal and distal members 19 and 15, respectively and a pair of guide rails 27 which cooperate to align the body portion 12 during longitudinal translation of the proximal 19 and distal members 15 relative to one another upon movement of handles 13 and 14. In the drawings and in the description which follows, the term "proximal", as is traditional, will refer to the end of the forceps 10 which is closer to the user, while the term "distal" will refer to the end which is further from the user.

Body portion 12 also includes a rotating member 50 which is preferably coupled to the proximal member 19 of the body portion 12 and a guide sleeve 35 which is coupled to handle 14. An electrical interface or plug 16 is preferably disposed within the proximal member 19 of the body portion 12 and receives a complimentary electrical interface (not shown) attached to the distal end of a cable 18 such that electrosurgical energy can be transferred from an electrical source to the forceps 10. A mechanical release 17 can be incorporated with plug 16 to releasably secure the cable 18 to the body portion 12.

As best shown in FIG. 3, the forceps 10 further includes an outer shaft 24 and a threaded connection 26 both of which are removably attached to the distal member 15 of the body portion 12. The outer shaft 24 incorporates a sealing gasket 28 for sealing a reciprocating inner insulated shaft 30. Inner shaft 30 is also removably attached to the guide sleeve 35 of the body portion 12 by way of a threaded connection 32 and is adapted for reciprocating longitudinal movement along the body portion 12 when handle 14 is moved relative to handle 13. More particularly, proximal movement of handle 14 moves the guide sleeve 35 and the inner shaft 30 towards proximal member 19 to allow a pair of coagulating jaws 20 to open to receive tissue. This will be explained in more detail below with respect to the operation of the instrument.

The coagulating jaws 20 and an associated rod-like electrode 22 are removably attached to the body portion 12 and extend distally therefrom. The electrode 22 (FIG. 6) is disposed within a central lumen of inner shaft 30 and extends proximally beyond inner shaft 30, through an aperture 25 disposed within the rotating member 50 and is rotatingly coupled to a lever 34 disposed therein. It is anticipated that various jaw configurations may be employed and/or interchange with electrode 22, e.g., The Kleppinger jaw, Hirsch Jaw, Tweezer jaw and/or the Insulated Tweezer jaw all sold by VALLEYLAB®, a subdivision of United States Surgical Corporation located at 5920 Longbow Drive, Boulder, Colo. 80301-3299.

Figure 7:
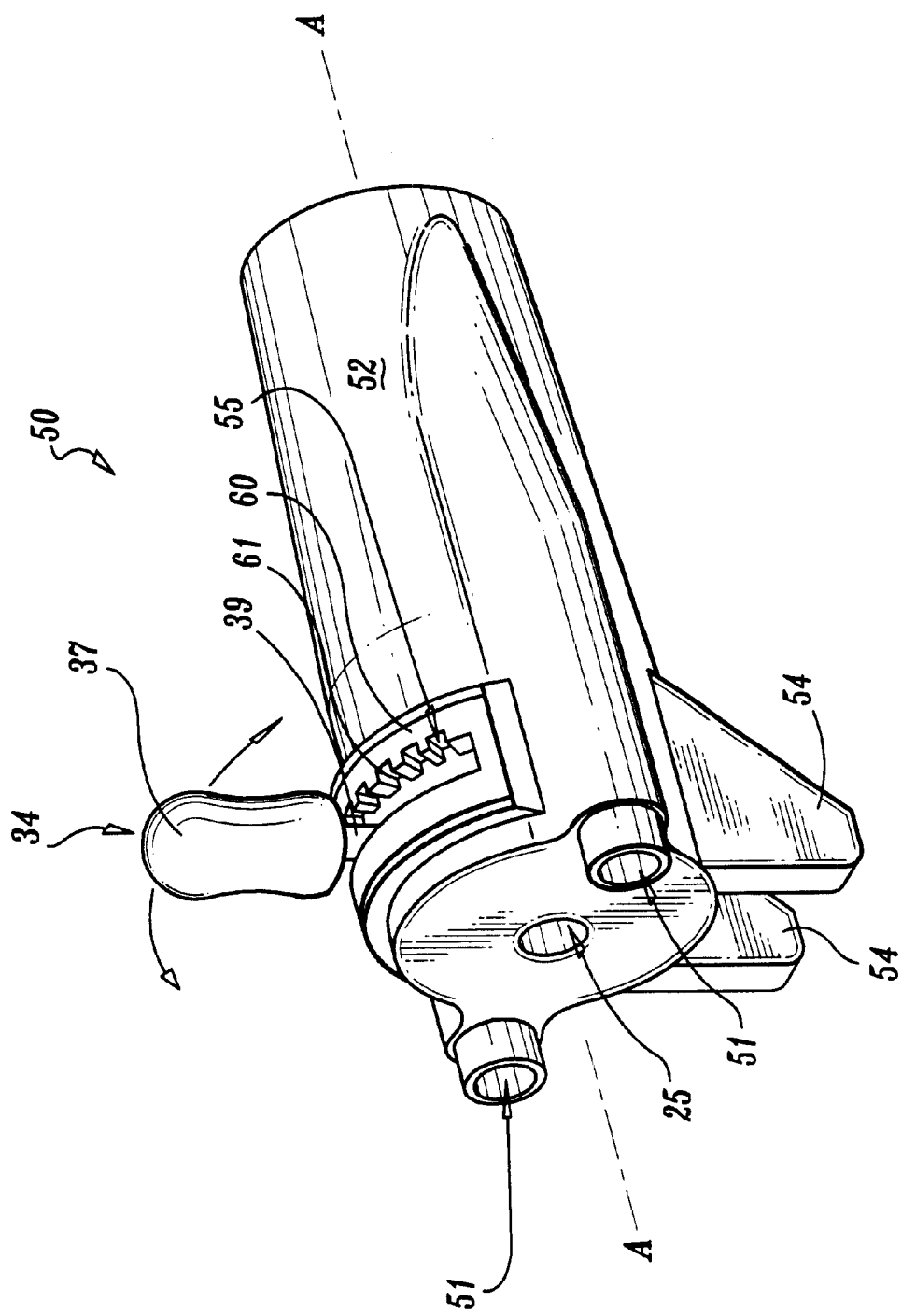
FIG. 7 is an enlarged, perspective view of a rotating and release member of the bipolar forceps of FIG. 1.
Figure 8:
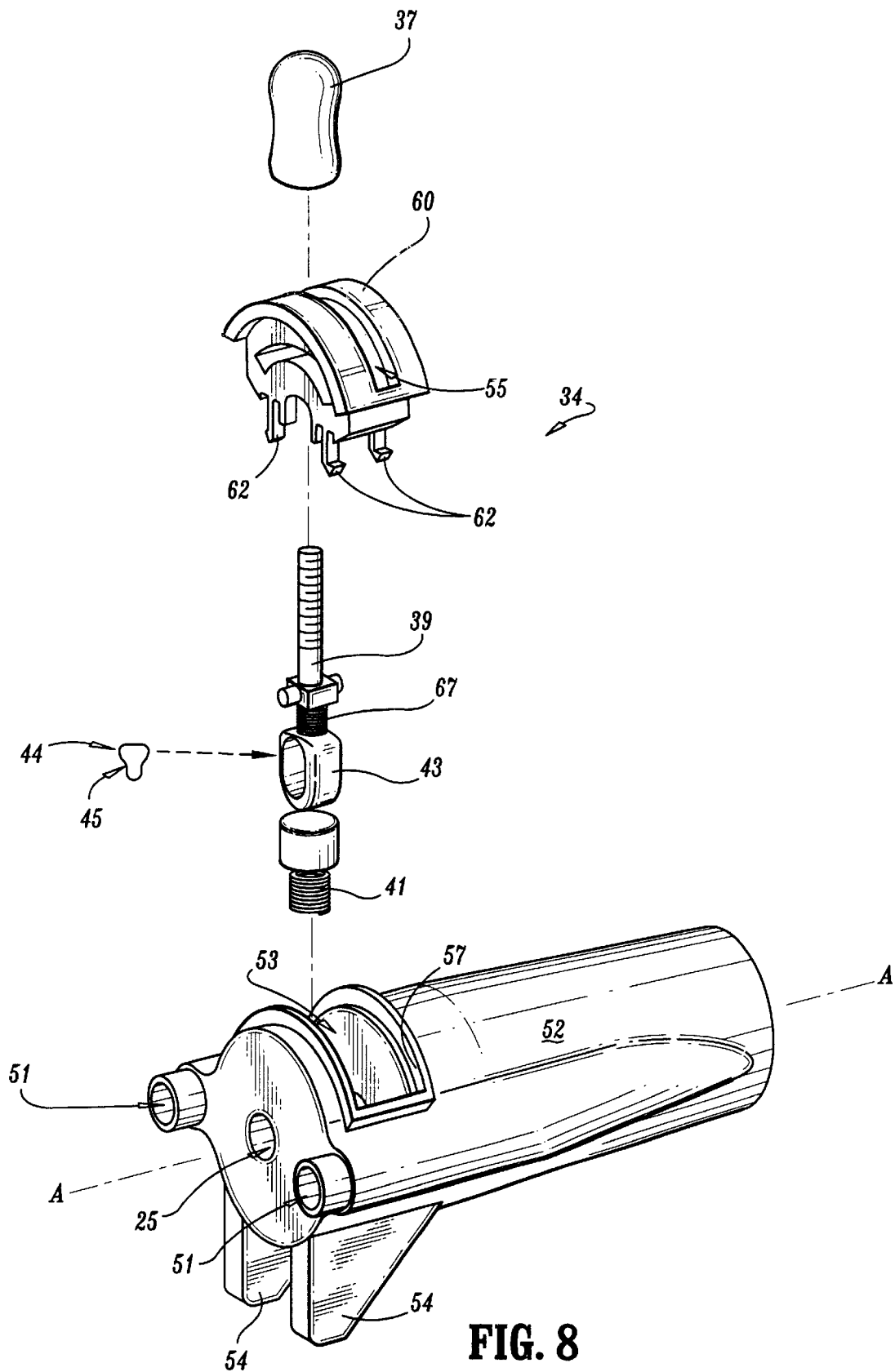
FIG. 8 is an enlarged, perspective view with parts separated of the rotating and release member of FIG. 7.

As best seen in FIGS. 7 and 8, the rotating member 50 includes a housing 52 which forms a part of the body portion 12. Portion 52 includes a pair of collars 51 for anchoring the proximal ends of the guide rails 27 and a pair of flanges 54 which are dimensioned to removably engage handle 13. It is envisioned that flanges 54 engage handle 13 about pin 59, however, flanges 54 can engage handle 13 in a different manner, e.g., snap-fit or press fit. Rotatable member 50 also includes a guide clip 60 which mechanically engages a corresponding groove 53 located proximate the upper half of housing 52. Preferably, guide clip 60 includes a plurality of resilient mechanical appendages or arms 62 which engage a rim 57 disposed about the inner periphery of groove 53 to removably couple the guide clip 60 to the groove 53.

Guide clip 60 includes an arcuatly-shaped channel 55 disposed therein which is sufficiently dimensioned to receive lever 34 in such a manner to allow arcuate movement of level 34 along slot 55 about a longitudinal axis "A" disposed through the housing 52 and the body portion 12. More particularly and as best shown in FIG. 8, lever 34 includes an elongated shaft 39 having an insulated knob 37 located at the upper end of the lever 34, a spring 41 located at the opposite end of the lever 34 and a coupling member 43 disposed therebetween. Coupling member 43 includes an elongated cuff 45 disposed therethrough which receivably engages electrode 22 such that arcuate movement of lever 34 within channel 55 imparts rotational movement to electrode 22 which, in turn, imparts rotational movement to the coagulating jaws 20.

It is envisioned that rotatable lever 34 can rotate electrode 22 and, therefore, coagulating jaws 20, about 120 degrees or about 60 degrees on either side of longitudinal axis "A". It is contemplated that the rotatable lever 34 can be spring biased to return to a 0 degree orientation relative to longitudinal axis "A" upon release by the user. It is also contemplated that the rotatable lever 34 can be unbiased and lever 34 is dimensioned to remain in frictional engagement within channel 55 upon arcuate movement thereof. It is further contemplated that guide clip 60 can include a plurality of notches 61 separated into discrete, degree graduations which allow a user to lock the lever 34 and, in turn, the jaws 20, at a specific rotational orientation.

Other embodiments can include a plurality of interchangeable guide clips 60 which restrict rotational movement of the lever 34 to a preset maximum angle which could be more or less than about 60 degrees in either direction about longitudinal axis "A". In addition, it is also contemplated to manufacture an interchangeable guide clip 60 which restricts rotational movement of the jaws 20 to one side of the longitudinal axis "A".

Uncoupling electrode 22 from body portion 12 is accomplished by depressing rotatable lever 34 which causes electrode 22 to be released distally from housing 52 of body portion 12. As mentioned above, electrode 22 extends proximally beyond inner shaft 30, through an aperture 25 disposed within rotating member 50 and is rotatingly coupled to lever 34 disposed therein. Lever 34 preferably includes a spring-like release mechanism 41 which, when depressed, disengages elongated cuff 45 from slots 21 on electrode 22 permitting free disengagement with the rotating member 50 through aperture 44. Upon release, spring 41 returns lever 34 to its normal biased position which locks electrode 22 within coupling member 43 elongated cuff 45. More particularly, upon release of lever 34, coupling member 43 moves up causing elongated cuff 45 to mechanically lock into slots 21 on electrode 22 locking electrode 22 to the rotating member 50. Depressing knob 37 and coupling member 43 unlocks elongated cuff 45 from slots 21 and allows a user to disengage the electrode 22 from the rotating member 50, i.e., slide electrode out from aperture 25 for cleaning or other purposes. It is envisioned that various other types of locking and release mechanisms can be incorporated with lever 34 to releasably engage electrode 22 to the rotating member 50, e.g., a hook and latch mechanism, a push button mechanism, a pull-up knob, or a screw.

Preferably, coagulating jaws 20 are normally biased in an open tissue receiving position and are held in a closed position as shown in FIGS. 1 and 3 by the distal end portion of inner shaft 30. More particularly, the coagulating jaws 20 move relative to one another in response to movement of handle 14 relative to handle 13; i.e., coagulating jaws 20 move from a normal, clamping position wherein the jaws 20 cooperate to grasp tissue therebetween to an open position wherein the jaws 20 are disposed in spaced relation relative to one another to receive tissue.

In operation, the rotatable bipolar forceps 10 is positioned in proximity of the body tissue to be coagulated, cut and/or sealed and rotated to the desired position. Handle portion 14 is then actuated proximally to slide inner shaft 30 in a proximal direction which releases coagulating jaws 20 from the distal end of inner shaft 30. Once freed from the inner shaft 30, jaws 20 open to receive tissue between the two opposing jaw surfaces. It is envisioned that jaws 20 are spring-biased in an open configuration to facilitate engagement of the tissue therebetween. Upon release of actuating handle 14, inner shaft 30 returns to its distal most position which causes jaws 20 to close about the tissue. Coagulation and/or cutting of tissue disposed between the coagulating jaws 20 can then be performed. It is envisioned that a switch, e.g., a foot switch or control panel (not shown), can be employed to selectively activate the electrode 22 once positioned.

It is envisioned that the rotatable bipolar forceps 10 can be completely disassembled for cleaning, sterilization and reuse. More particularly, when electrical connection, i.e., plug 16, is removed from the proximal member 19 of body portion 12, electrode 22 and coagulating jaws 20 can be detached from body portion 12 by depressing lever 34. Outer shaft 24 and inner shaft 30 both include connecting screws 26 and 32, respectively, for detaching the shafts 24, 30 from body portion 12.

In some cases it may be preferable to include a ratchet and pawl system to segment the movement of the two handles 13, 14 into discrete units which will, in turn, impart discrete movement to the coagulating jaws 20 relative to one another.

From the foregoing and with reference to the various figure drawings, those skilled in the art will appreciate that certain modifications can also be made to the present disclosure without departing from the scope of the present disclosure. For example, although it is preferable to vertically align coagulating jaws 20 relative to one another, in some cases it may be preferable to offset the jaws 20 relative to one another either longitudinally or transversely to suit a particular purpose.

Moreover, although it is preferable to manufacture the rotating member 50 such that arcuate movement of the lever 34 across longitudinal axis "A" directly translates into substantially similar movement of the electrode 22 about axis "A", it is contemplated that a gearing system, transmission system and/or the like can be incorporated into the rotating member 50 to increase or decrease the rotational ratio between the lever 34 and the electrode 22, e.g., 2:1, 3:1, to provide greater control to the user. Moreover, it is also envisioned that the lever 34 can be incorporated with a gearing system, pulley system or the like such that longitudinal movement of the lever 34 along axis "A" translates into rotational movement of the electrode about longitudinal axis "A".

Still, further, it is envisioned that rotating member 50 and the internal components associated therewith can be manufactured such that lever 34 not only controls the rotational movement of the electrode 22 about longitudinal axis "A" but also controls limited translational movement of the electrode 22 along longitudinal axis "A" which may be suited for a particular purpose.

It is envisioned that the various internal components of the rotatable forceps can be quickly and easily disassembled after use for sterilization and cleaning purposes without jeopardizing the efficacy of the electrodes and the insulation. Once sterilized and cleaned, the forceps can be quickly and easily reassembled for reuse.

While only one embodiment of the disclosure has been described, it is not intended that the disclosure be limited thereto, as it is intended that the disclosure be as broad in scope as the art will allow and that the specification be read likewise. Therefore, the above description should not be construed as limiting, but merely as exemplications of a preferred embodiment. Those skilled in the art will envision other modifications within the scope and spirit of the claims appended hereto.

What is claimed is:

1. A rotatable bipolar forceps, comprising:
    a body portion defining a longitudinal axis;
    an electrode selectively removable from the body portion; the electrode connecting a pair of jaws to a source of electrical energy;
    a shaft extending from the body portion;
    at least one handle attached to the body portion for imparting movement to the shaft which causes the jaws to move from a first open position wherein the jaws are disposed in spaced relation relative to one another to a second clamping position wherein the jaws are moved closer together to grasp tissue therebetween; and
    a rotating member cooperating with the electrode; the rotating member rotating the electrode and the jaws relative to the longitudinal axis of the body portion and releasably coupling the electrode to the body portion.

2. A rotatable bipolar forceps according to claim 1 wherein the shaft further comprises:

an outer shaft removably coupled to the body portion; and an inner shaft disposed within the outer shaft which is movable relative to the outer shaft upon movement of the handle, the inner shaft being dimensioned to house the electrode therein.

3. A rotatable bipolar forceps according to claim 2 wherein the inner shaft is removably coupled to the body portion.

4. A rotatable bipolar forceps according to claim 2 wherein the inner shaft is insulated.

5. A rotatable bipolar forceps according to claim 2 wherein movement of the inner shaft relative to the outer shaft causes the jaws to move from the first position to the second position.

6. A rotatable bipolar forceps according to claim 1 wherein the rotating member includes a lever which couples to a distal end of the electrode, the lever for imparting rotational movement to the electrode and the jaws.

7. A rotatable bipolar forceps according to claim 6 wherein the lever rotates the electrode and the jaws about 60 degrees on either side of the longitudinal axis.

8. A rotatable bipolar forceps according to claim 6 wherein the rotating member further includes a guide clip which selectively couples to the body portion to control the rotational movement of the lever.

9. A rotatable bipolar forceps according to claim 8 wherein the guide clip includes an arcuate-shaped slot disposed therein for controlling the rotational movement of the lever.

10. A rotatable bipolar forceps according to claim 8 wherein the guide clip includes a plurality of graduations for releasably locking the lever at various locations during rotation.

11. A rotatable bipolar forceps according to claim 6 wherein the body portion further includes a groove which selectively receives any one of a series of interchangeable guide clips each having differently-shaped slots disposed therein for controlling the rotational movement of the lever.

12. A rotatable bipolar forceps according to claim 6 wherein the lever is mechanically coupled to the electrode.

13. A rotatable bipolar forceps according to claim 6 wherein the lever is biased in a substantially normal position relative to the longitudinal axis.

14. A rotatable bipolar forceps according to claim 13 wherein the lever includes a spring which biases the lever in the normal position.

15. A rotatable bipolar forceps according to claim 6 whne the lever includes a spring release member which operates to selectively couple the distal end of the electrode to the lever.

16. A rotatable bipolar forceps according to claim 15 wherein a force applied against the spring release member disengages the electrode from the rotating member.

17. A rotatable bipolar forceps according to claim 6 wherein the body portion further comprises an aperture located substantially therethrough and the lever further comprises an aperture which aligns with the body aperture to receive said electrode therethrough.

18. A rotatable bipolar forceps according to claim 17 wherein the lever further includes a spring release member aperture with the body aperture to allow movement of the electrode for assembly or disassembly when a force is applied against the spring release member.

19. A rotatable bipolar forceps according to claim 18 wherein the body aperture and the spring release member aperture are substantially coaxial with the longitudinal axis when the force is applied against the spring release member.

\* \* \* \* \*